United States Patent
Towse et al.

(10) Patent No.: US 12,303,353 B2
(45) Date of Patent: *May 20, 2025

(54) DENTAL IMPLANT WITH CODED UPPER SURFACE

(71) Applicant: BIOMET 3I, LLC, Palm Beach Gardens, FL (US)

(72) Inventors: Ross W Towse, San Marcos, CA (US); Zachary B. Suttin, Jupiter, FL (US)

(73) Assignee: BIOMET 3I, LLC, Palm Beach Gardens, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/514,657

(22) Filed: Nov. 20, 2023

(65) Prior Publication Data

US 2024/0108443 A1     Apr. 4, 2024

Related U.S. Application Data

(63) Continuation of application No. 17/351,764, filed on Jun. 18, 2021, now Pat. No. 11,864,975, which is a continuation of application No. 14/248,667, filed on Apr. 9, 2014, now Pat. No. 11,065,090.

(60) Provisional application No. 61/810,106, filed on Apr. 9, 2013.

(51) Int. Cl.
*A61C 8/00*      (2006.01)
*A61C 13/00*     (2006.01)
*A61C 9/00*      (2006.01)
*G16H 20/40*     (2018.01)

(52) U.S. Cl.
CPC ............ *A61C 8/009* (2013.01); *A61C 8/0022* (2013.01); *A61C 8/006* (2013.01); *A61C 13/0004* (2013.01); *A61C 9/0053* (2013.01); *G16H 20/40* (2018.01)

(58) Field of Classification Search
CPC ....... A61C 8/009; A61C 8/0022; A61C 8/006; A61C 9/0053; A61C 13/0004
USPC .................................................. 433/172–176
See application file for complete search history.

(56) References Cited

U.S. PATENT DOCUMENTS

| | | | | |
|---|---|---|---|---|
| 4,011,602 | A * | 3/1977 | Rybicki | A61F 2/3662 606/76 |
| 5,350,301 | A * | 9/1994 | De Buck | A61C 8/0066 433/173 |
| 5,729,464 | A * | 3/1998 | Dimitri | G11B 17/225 |
| 6,406,295 | B1 * | 6/2002 | Mahler | A61C 8/0001 433/173 |
| 8,185,224 | B2 * | 5/2012 | Powell | A61C 8/00 700/95 |

(Continued)

FOREIGN PATENT DOCUMENTS

| | | | | |
|---|---|---|---|---|
| EP | 1006529 A2 * | 6/2000 | | G11B 23/38 |
| WO | WO-2011078560 A2 * | 6/2011 | | A61C 13/0004 |

*Primary Examiner* — Matthew M Nelson
(74) *Attorney, Agent, or Firm* — Sheridan Ross P.C.

(57) ABSTRACT

A dental implant for insertion into bone within a patient's mouth comprises a body and a scannable code. The body includes a bone-engaging exterior surface, an anti-rotational feature for non-rotationally mating with an abutment, and an upper region. The upper region includes an upper surface for engaging the abutment. The scannable code on the upper surface provides information concerning the dental implant. The information includes at least two features of the dental implant.

21 Claims, 2 Drawing Sheets

(56) References Cited

U.S. PATENT DOCUMENTS

| | | | | |
|---|---|---|---|---|
| 8,197,535 B2* | 6/2012 | Gladdish, Jr. | A61L 31/18 | 623/1.34 |
| 8,944,818 B2* | 2/2015 | Robb | A61C 8/0048 | 433/172 |
| 11,864,975 B2* | 1/2024 | Towse | A61C 8/009 | |
| 2002/0061701 A1* | 5/2002 | Chan | A63H 33/00 | 446/175 |
| 2004/0191727 A1* | 9/2004 | Shelemay | A61L 27/56 | 433/173 |
| 2006/0019219 A1* | 1/2006 | Saliger | A61C 8/0001 | 433/173 |
| 2006/0172250 A1* | 8/2006 | Wen | A61C 7/00 | 433/18 |
| 2007/0092854 A1* | 4/2007 | Powell | A61C 13/0004 | 433/213 |
| 2007/0281279 A1* | 12/2007 | Chander | A61C 8/0001 | 433/173 |
| 2008/0206709 A1* | 8/2008 | Lannan | A61C 8/005 | 433/172 |
| 2008/0254411 A1* | 10/2008 | Bondar | A61C 8/0001 | 433/174 |
| 2009/0155744 A1* | 6/2009 | Jandali | A61C 8/00 | 433/174 |
| 2009/0325127 A1* | 12/2009 | Kusch | A61C 13/0004 | 700/98 |
| 2011/0200968 A1* | 8/2011 | Laizure, Jr. | A61C 8/008 | 433/201.1 |
| 2012/0189982 A1* | 7/2012 | Powell | B29C 64/386 | 433/201.1 |
| 2012/0264081 A1* | 10/2012 | Philibin | A61C 8/008 | 433/173 |
| 2012/0295223 A1* | 11/2012 | Robb | A61C 9/004 | 433/173 |
| 2013/0108985 A1* | 5/2013 | Amber | A61C 8/005 | 433/173 |
| 2013/0110117 A1* | 5/2013 | Soliman | A61B 17/1728 | 606/96 |
| 2013/0189646 A1* | 7/2013 | Hochman | A61C 19/04 | 433/174 |
| 2013/0196290 A1* | 8/2013 | Herrington | A61C 8/0001 | 433/173 |
| 2013/0209956 A1* | 8/2013 | Sanders | A61C 8/0043 | 433/173 |
| 2013/0216976 A1* | 8/2013 | Ihde | A61C 8/0024 | 433/174 |
| 2013/0252205 A1* | 9/2013 | Worthington | A61C 8/0075 | 433/173 |
| 2013/0260336 A1* | 10/2013 | Bondar | A61C 8/0048 | 433/173 |
| 2013/0260339 A1* | 10/2013 | Reddy | A61C 8/0068 | 433/174 |
| 2014/0234801 A1* | 8/2014 | Herrington | A61C 13/0004 | 703/1 |
| 2014/0302458 A1* | 10/2014 | Towse | A61C 8/006 | 703/1 |
| 2015/0037757 A1* | 2/2015 | Kwan | A61C 13/0004 | 433/174 |
| 2017/0238792 A1* | 8/2017 | Yokota | A61B 1/00165 | |
| 2018/0110403 A1* | 4/2018 | Okazaki | A61B 17/3478 | |
| 2018/0170423 A1* | 6/2018 | Wada | B62D 5/0481 | |

* cited by examiner

DENTAL IMPLANT WITH CODED UPPER SURFACE

CROSS-REFERENCE TO RELATED APPLICATIONS

This application is a continuation of U.S. patent application Ser. No. 17/351,764, filed Jun. 18, 2021, now U.S. Pat. No. 11,864,975, which is a continuation of U.S. patent application Ser. No. 14/248,667, filed Apr. 9, 2014, now U.S. Pat. No. 11,065,090, which claims the benefit of and priority to U.S. Provisional Patent Application No. 61/810,106 titled "Dental Implant With Coded Upper Surface" and filed on Apr. 9, 2013, all of which are incorporated herein by reference in their entirety.

FIELD OF THE INVENTION

The present invention relates generally to an abutment system for a dental implant system. More particularly, the present invention relates to a dental implant having an upper surface that is coded to provide details about the dental implant.

BACKGROUND OF THE INVENTION

The dental restoration of a partially or wholly edentulous patient with artificial dentition is typically done in two stages. In the first stage, an incision is made through the gingiva to expose the underlying bone. An artificial tooth root, in the form of a dental implant, is placed in the jawbone for osseointegration. The dental implant generally includes a threaded bore to receive a retaining screw for holding mating components thereon. During the first stage, the gum tissue overlying the implant is sutured and heals as the osseointegration process continues.

Once the osseointegration process is complete, the second stage is initiated. Here, the gingival tissue is re-opened to expose an end of the dental implant. A healing component or healing abutment is fastened to the exposed end of the dental implant to allow the gingival tissue to heal therearound. It should be noted that the healing abutment can be placed on the dental implant immediately after the implant has been installed and before osseointegration. In some situations, the osseointegration step and gingival healing steps have been combined into a one-step process. Alternatively, instead of a healing abutment, a temporary abutment may be used to support a temporary prosthesis and also serves the purpose of shaping the gingiva above the dental implant, just like a healing abutment.

In more recent years, scanning technologies have been used to aid in the development of permanent prostheses. The scanning technologies are used to locate the underlying dental implant to which the final prosthesis is supported, as well as the adjacent soft tissue, the adjacent dentition, and the opposing dentition. The present disclosure is directed to a coding system on the dental implant that provides information that can be acquired via an intra-oral scan to gain information about the underlying implant.

SUMMARY OF THE INVENTION

In one aspect, a dental implant for insertion into bone within a patient's mouth comprises an implant body and a scannable code. The body includes a bone-engaging exterior surface, an anti-rotational feature for non-rotationally mating with an abutment, and an upper region. The upper region includes an upper surface for engaging the abutment. The scannable code on the upper surface provides information concerning an angular orientation of the anti-rotational feature and a size dimension of the dental implant.

In another aspect, the present invention is a dental implant for insertion into bone within a patient's mouth, comprising an implant body and a scannable code. The body includes a bone-engaging exterior surface, an anti-rotational feature for non-rotationally mating with an abutment, and an upper region. The upper region includes an upper surface for engaging the abutment. The scannable code on the upper surface provides information concerning the dental implant. The information including at least two features of the dental implant In a further aspect, the present invention is a method of using a dental implant that has been placed in bone within the mouth of a patient. The method comprises (i) scanning the mouth including an upper surface of the dental implant so as to acquire scan data corresponding to a scannable code on the upper surface, (ii) developing a virtual model of at least a portion of the mouth of the patient, and (iii) using the scan data to locate a virtual implant within the virtual model.

The above summary is not intended to represent each embodiment or every aspect of the present disclosure. Rather, the summary merely provides an exemplification of some of the novel features presented herein. The above features and advantages, and other features and advantages of the present disclosure, will be readily apparent from the following detailed description of exemplary embodiments and best modes for carrying out the present invention when taken in connection with the accompanying drawings and the appended claims.

BRIEF DESCRIPTION OF THE DRAWINGS

The foregoing and other advantages of the invention will become apparent upon reading the following detailed description and upon reference to the drawings.

Figure 1:
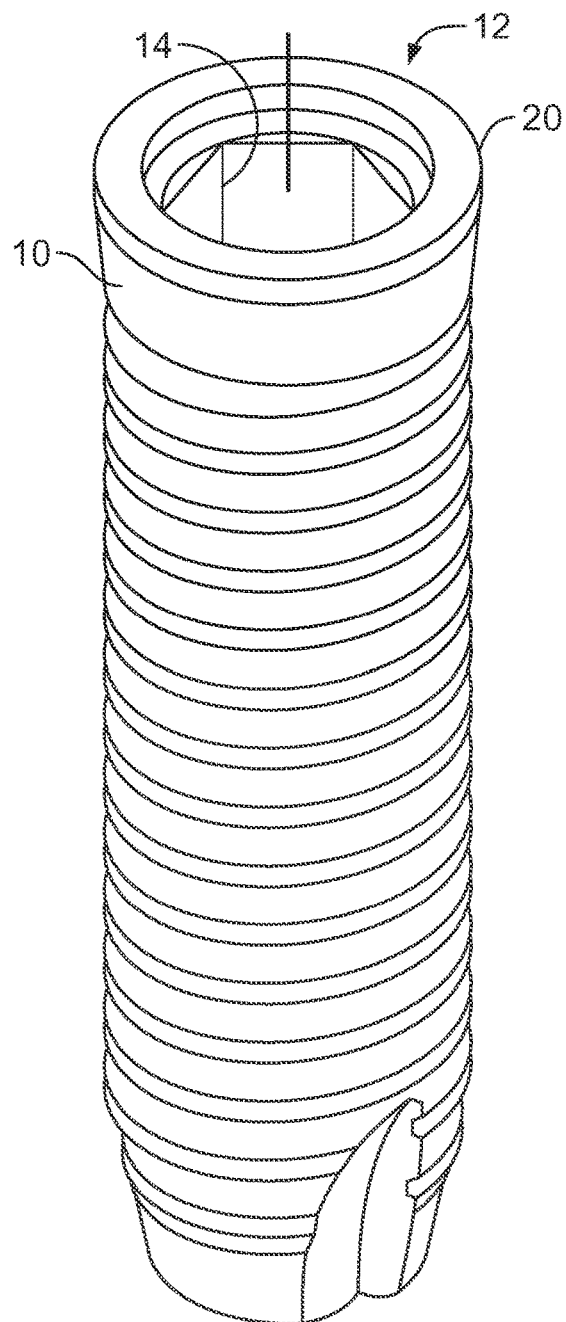
FIG. 1 is a perspective view of a dental implant.

While the present disclosure is susceptible to various modifications and alternative forms, specific embodiments have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DESCRIPTION OF ILLUSTRATIVE EMBODIMENTS

Figure 2:
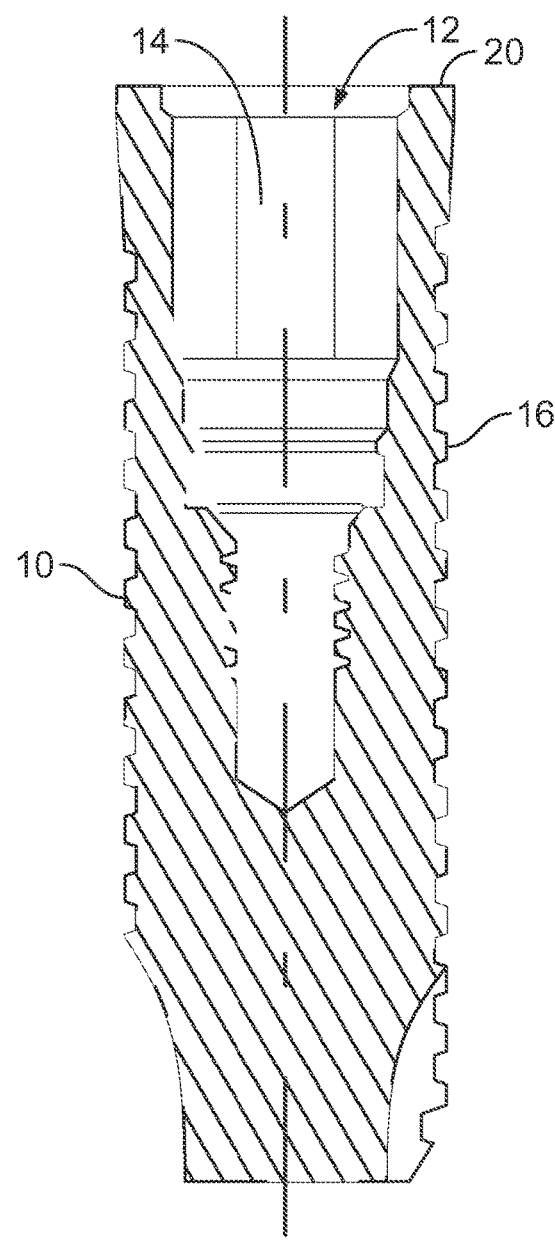
FIG. 2 is a side cross-sectional view of the dental implant of FIG. 1.

Referring to FIGS. 1 and 2, a dental implant 10 includes a bore 12 with an anti-rotational section 14 and a threaded section 16. The anti-rotational section 14 is shown as a hexagonal socket, although several other types of anti-rotational features (both internal and external) can be used on the dental implant 10. The upper portion of the dental implant 10 includes a table 20, which is an upper surface (e.g., the uppermost surface for dental implants with an internal connection) that engages an abutment that is mated with the dental implant 10. The abutment would be held on the dental implant 10 via a screw that engages the threaded section 16 of the dental implant 10.

Figure 3A:
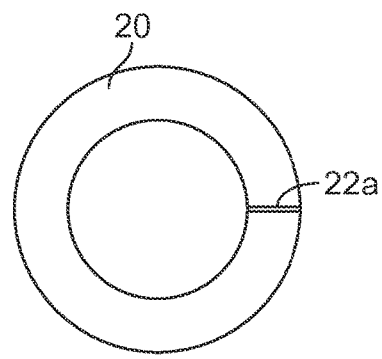
FIG. 3A illustrates a view of the upper surface of a dental implant having a first type of code.
Figure 3B:
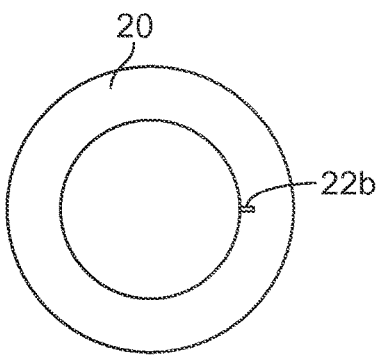
FIG. 3B illustrates a view of the upper surface of a second dental implant have the first type of code.
Figure 3C:
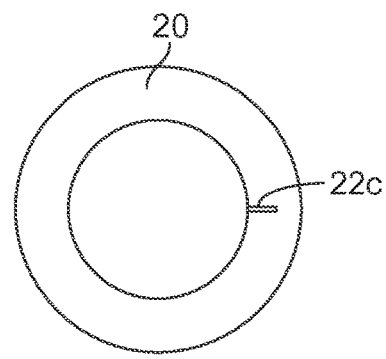
FIG. 3C illustrates a view of the upper surface of a third dental implant have the first type of code.

FIGS. 3A-3C illustrate a scannable code on the upper surface 20 of the dental implant 10. The scannable code is a radially extending marker 22 that is used to provide information related to the dental implant 10. The radially extending marker 22 can also be of different lengths to provide additional information. For example, the radially extending marker 22a having a first length (FIG. 3A) can be indicative of a first feature of the dental implant, the radially extending marker 22b having a second length (FIG. 3B) can be indicative of a second feature of the dental implant, and the radially extending marker 22c having a third length (FIG. 3C) can be indicative of a third feature of the dental implant. For example, each of the markers 22a, 22b, 22c can indicate the location of one flat of the anti-rotational section 14 so that the implant's angular orientation and, hence, the angular orientation of the anti-rotational section 14 is known. The length of the radially extending markers 22a, 22b, and 22c may indicate a dimension of the implant, such as its length or diameter of the upper surface 20. In short, the radially extending markers 22a, 22b, and 22c are codes that are indicative of one or more features of the dental implant 10.

Figure 4A:
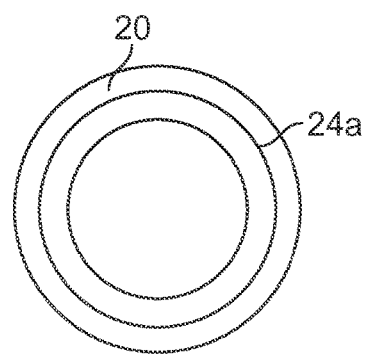
FIG. 4A illustrates a view of the upper surface of a first dental implant having a second type of code.
Figure 4B:
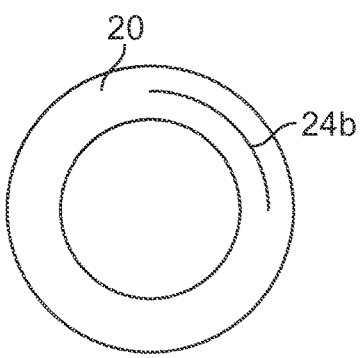
FIG. 4B illustrates a view of the upper surface of a second dental implant having the second type of code.
Figure 4C:
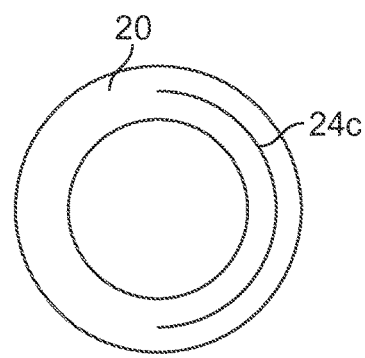
FIG. 4C illustrates a view of the upper surface of a third dental implant having the second type of code.

FIGS. 4A-4C illustrate a second type of scannable code on the upper surface 20 of the dental implant 10. The scannable code is a circumferentially extending marker 24 that is used to provide information related to the dental implant 10. The circumferentially extending marker 24 can also be of different lengths to provide additional information. For example, the circumferentially extending marker 24a having a first length (360 degrees in FIG. 4A) can be indicative of a first feature of the dental implant, the circumferentially extending marker 24b having a second length (90 degrees in FIG. 4B) can be indicative of a second feature of the dental implant, and the circumferentially extending marker 24c having a third length (180 degrees in FIG. 4C) can be indicative of a third feature of the dental implant. Of course, the circumferential length can be broken down in terms of 30-degree segments or 60-degree segments, as opposed to the 90-degree segments suggested by FIGS. 4A-4C. The length of the circumferentially extending markers 24a, 24b, and 24c may indicate a dimension of the implant, such as its length or diameter of the upper surface 20. The circumferentially extending markers 24a, 24b, and 24c can also be used to identify the central axis of the implant 10 because each would have a radius of curvature that is centered around the central axis. Hence, the circumferentially extending markers 24a, 24b, and 24c help define the coordinate system used for the prosthetic restoration. In short, the circumferentially extending markers 24a, 24b, and 24c are codes that are indicative of one or more features of the dental implant 10.

Figure 5A:
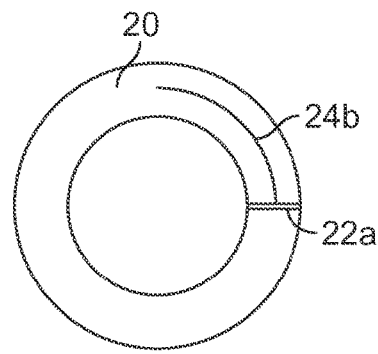
FIG. 5A illustrates a view of the upper surface of a first dental implant having a combination of the first type of code and the second type of code.
Figure 5B:
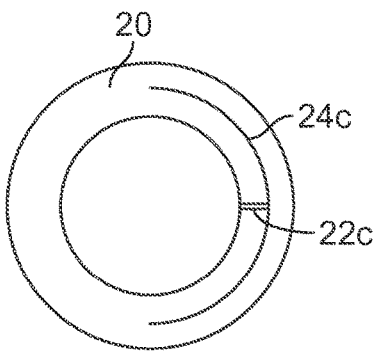
FIG. 5B illustrates a second view of the upper surface of a second dental implant having a combination of a first type of code and a second type of code.

FIGS. 5A-5B illustrate the use of a combination of the radially extending markers 22 on FIG. 3 and the circumferentially extending markers 24 of FIG. 4 that are used to provide information related to the dental implant 10. The circumferentially extending markers 24 may indicate a first dimension of the implant, such as its diameter, while the radially extending markers 22 can be indicative of a second dimension of the implant, such as its length. Additionally, each of the radially extending markers 22 can indicate the location of one flat of the anti-rotational section 14 so the implant's angular orientation and, hence, the angular orientation of the anti-rotational section 14 is known. In short, the combination of the circumferentially extending markers 24 and radially extending markers 22 present a code that is indicative of one or more features of the dental implant 10.

The circumferentially extending markers 24 and radially extending markers 22 can be placed on the upper surface in several ways. For example, they can be etched or printed (e.g. laser etching or laser printing) on the upper surface 20 or they may developed by a micro-grooving process.

Figure 6:
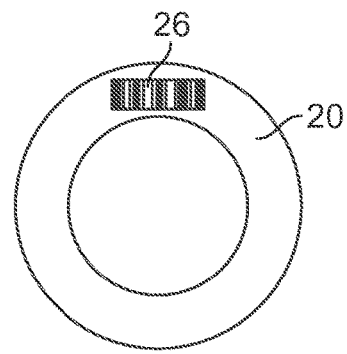
FIG. 6 is a view of the upper surface of the dental implant having a third type of code.

Of course, other types and shapes of information markers are possible on the upper surface 20 of the dental implant 10. For example, FIG. 6 illustrates the use of a bar-code marker 26 that can provide several detailed pieces of information once the scanning system has read the code on the bar-code marker 26. The information markers could include discrete scannable symbols, such as a "+" symbol, a "−" symbol, a "o" symbol, and a "A" symbol (etched or printed on the upper surface). Additionally, the presence or absence of each discrete symbol can be thought of as "1" or a "0" in a certain location on the upper surface 20, such that the orientations markers present, as a group, a code that is akin to a binary code of 1's and 0's. The unique code for each implant would be used to identify it. Any of these codes can be used in conjunction with or in combination with the markers 22 and 24 of FIGS. 3-5.

In addition to the aforementioned information regarding the implants, the codes can also provide the location of the table 20 (the uppermost surface) of the implant 10, the type of implant (e.g. its type of internal connection), the type of implant including its bone-interfacing surface technology (e.g., acid-etched, grit-blasted, nano-etched, nano-particles, etc.), the basic catalog information, and the implant manufacturer's identity. Additionally, various markers or symbols (e.g., an arrow marker or diamond marker) can be added to the upper surface to identify one of the flat surfaces of the anti-rotation feature 14. Also, the scannable code can be used to indicate if the implant 10 is of a type that is normally platform-switched (e.g., an implant 10 that has a slight bevel at its periphery on the upper surface 20, where the abutment does not engage the bevel and may be diametrically smaller than the max diameter of the upper surface 20).

Other types of coded systems could be used instead of the system that is discussed with reference to FIGS. 3-6. For example, the same symbol at different locations on the surface of the upper surface 20 could identify the unique implant 10. For example, the upper surface 20 of the implant 10 can be segmented into twelve regions, wherein each 30° segment has a geometrical pie shape, like hour segments on a clock. A single orientation line is present at one angular location, e.g., at 12 o'clock, and is used for locating the anti-rotational surface of the underlying implant 120 as well as setting the circumferential order of the twelve segments. A single type of information marker (e.g., a "A" symbol) can be placed at one of the twelve segments on the top surface, with each of the twelve segments corresponding to one of twelve possible implants 10 having a known size (length and diameter). Of course, the discrete locations can be more or less than twelve, depending on the number that is needed. And, the discrete locations may include different radially spaced locations, and not just circumferentially spaced locations. Yet further, a combination of discrete locations and specific types of symbols can increase the potential number of options (i.e., a "+" symbol at circumferential segment #1 of 12 is implant "A", but a "Δ" symbol at circumferential segment #1 of 12 is implant "B"). Accordingly, the location of a single type (or multiple types) of information marker within one of several distinct locations on the upper surface 20 provides a coded system to identify the underlying implant 10, and the scanning process can easily identify the information marker and its location.

In addition to the unique codes being defined by symbols or markings, the codes for defining the dimensions of the healing cap 24 can be presented in the form of different colors (or combinations thereof) that define one or more features of the dental implant. Because the resolution and the photo-realistic data capture of the current intra-oral scanning systems and method has improved, these colors markers can be readily identified, such that the identification of implant 10 can be achieved. Accordingly, intra-oral scanning of the implant 10 may capture scan data corresponding to a unique combination of color(s), symbol(s), and/or other markings from the implant that serves as a code (or part of a code) for identifying the particular implant 10.

Further, because the data acquisition capabilities of current intra-oral scanning systems and methods has improved, the upper surface of the implant 10 can be scanned and shape-matched to help identify the implant to its diametric dimension. In other words, the actual diametric size of the upper surface 20 serves as part of the information that is used to identify the implant 10. The location of any information marker on the upper surface 20 relative to the scanned circumference of the upper surface 20 provides an informational combination that can be matched against library of implants to identify the specific implant 10 that has been scanned. The markers (e.g., a "Δ" symbol or a "o" symbol or a circumferentially extending markers) can have the same size on all diametric sizes of the implants, such that the relative dimensions of the information marker to each implant's diameter is different, which assists with the shape-matching algorithm.

Alternatively, the scanning can rely on less than the entire upper surface 20 of the implant, such as when the gingiva begins to grow slightly over the implant 10. Hence, the markers may all reside within a radial distance that is less than 90%, 80%, or 75% of the overall diameter so that their ability to be viewed (i.e., scanned) within the scanning process is unimpeded.

In one method, after the dental implant 10 has been installed, a clinician may immediately scan the mouth and dental implant 10. Or, the implant 10 and mouth may be scanned to identify the conditions in the patient's mouth after the gingival tissue has healed around a healing abutment or temporary prosthesis. In this situation, the healing abutment or temporary prosthesis is removed prior to the scanning process, which reveals the subgingival contour leading down to the implant's upper surface 20. The scan data achieved in the scanning process includes the adjacent gingival tissue and, possibly, teeth. The scan data is used to develop a virtual model, which is typically displayed on a computer display. The scan data corresponding to the scannable code on the implant 10 is used to identify the type of dental implant and place a virtual implant at the correct position in the virtual model. The virtual implant may only need to be a portion of the actual implant, such as its upper surface and its anti-rotational feature. The virtual model is used to develop a patient-specific custom abutment and, possible an overall prosthesis that includes the abutment. In summary, a patient-specific custom abutment (and an overall prosthesis, which may include a patient-specific custom abutment) can be developed based on the information derived from the scannable code that produces (i) geometric and locational information for the implant 10 relative to the adjacent soft tissue structures and teeth (or a tooth) and (ii) the angular orientation of the implant's anti-rotational feature 14. Again, the intra-oral scanning may take place before, during, or after the gingival-healing period. Stated differently, the scannable code on the implant 10 provides information related to the prosthetic restoration's interface coordinate system, the seating diameter of the implant 10, the type of connection to the prosthesis, and the orientation of the anti-rotational connection—all of which are helpful in the virtual design process that is used in making a patient-specific custom abutment and the overall prosthesis.

While the illustrated embodiments have been primarily described with reference to the development of a patient-specific abutment for a single tooth application, it should be understood that the present invention is also useful in multiple-tooth applications, such as bridges and bars for supporting full or partial dentures. In those situations, the patient-specific abutment would not necessarily need a non-rotational feature for engaging the underlying implant(s) because the final prosthesis would also be supported by another structure in the mouth (e.g., one or more additional underlying implants), which would inherently achieve a non-rotational aspect to the design. In any event, using a scanning process to obtain the necessary information about the emergence profile shape of the gingiva and the dimensional and/or positional information for the implant(s) (via information markers in the temporary prosthetic assembly) can lead to the development of an aesthetically pleasing multiple-tooth system.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the present invention, which is set forth in the claims that follow.

What is claimed is:

1. A system of using scan data of a dental implant pre-positioned in bone within a mouth of a patient to develop a virtual model for use in a virtual design process, comprising:

a computer comprising a messaging input and output;

a data input configured to receive scan data of the mouth of the patient including a surface of the dental implant, the scan data including information corresponding to scanning of a scannable code on the surface of the dental implant, wherein the scannable code provides information regarding an anti-rotational feature of the dental implant;

a computer in communication with the messaging input that is configured to develop a virtual model of at least a portion of the mouth of the patient and uses the information corresponding to scanning of a scannable code to locate a position of a central axis of a virtual implant within the virtual model and an angular orientation of the anti-rotational feature in the virtual model.

2. The system of claim 1, wherein a plurality of scannable codes on a plurality of differently diametrically sized dental implants are commonly sized such that the relative dimensions of the scannable code to each dental implant's diameter is different and wherein the virtual implant is representative of at least a portion of the dental implant.

3. The system of claim 2, wherein the portion includes the surface and the anti-rotational feature of the dental implant.

4. The system of claim 1, wherein the scannable code includes a circumferentially extending marker.

5. The system of claim 4, wherein a radius of curvature of the circumferentially extending marker is centered around a central axis of the dental implant.

6. The system of claim 4, wherein the radius of curvature provides a position of the central axis of the dental implant.

7. The system of claim 4, wherein the scannable code includes a radially extending marker positioned on a location of the surface that is adjacent to the anti-rotational feature of the dental implant, and wherein the anti-rotational feature is an internal structure that is within a bore of the dental implant, the location of the radially extending marker provides a rotational orientation of the anti-rotational feature.

8. The system of claim 7, wherein the radially extending marker has a first length, the first length of the radially extending marker providing information of a first size dimension of the dental implant.

9. The system of claim 8, wherein the radially extending marker includes a second length, the second length of the radially extending marker providing information of a second size dimension of the dental implant.

10. The system of claim 1, wherein the scannable code includes a barcode marker and wherein the anti-rotational feature is located on a surface of a threaded bore of the dental implant.

11. The system of claim 1, wherein the scan data comprises geometric and locational information for the dental implant relative to an adjacent soft tissue structure and/or tooth, a seating diameter of the dental implant, and a type of connection of the dental implant to a prosthesis and further including a computer display configured to display the virtual model.

12. The system of claim 1, wherein the computer is further configured to develop, by use of the virtual model, a patient-specific custom abutment, wherein the scan data comprises information relative to an interface coordinate system of the patient-specific custom abutment, a seating diameter of the dental implant, a type of connection to the patient-specific custom abutment, and an orientation of an anti-rotational connection between the dental implant and custom abutment.

13. The system of claim 1, wherein the using comprises the computer determining a location of the scannable code on the surface of the dental implant relative to a scanned circumference of the surface of the dental implant and matching the determined location of the scannable code relative to the scanned circumference against a library of implants to identify the dental implant and further including developing, by use of the virtual model, a prosthesis to be placed on the dental implant.

14. The system of claim 1, wherein the information from the scannable code provides features about the dental implant placed in the mouth of the patient, wherein the scannable code comprises information relating to a seating diameter of the dental implant implant, and wherein the features comprise a type of connection of the dental implant to a prosthesis.

15. The system of claim 1, wherein the scannable code provides information for at least one feature of the dental implant and wherein the at least one feature of the dental implant comprises a type of connection of the dental implant to a prosthesis.

16. The system of claim 1, wherein the scannable code provides information for at least two features of the dental implant and wherein the anti-rotational feature is located on a surface of a threaded bore of the dental implant.

17. The system of claim 16, wherein the at least two features of the dental implant include a rotational orientation of the anti-rotational feature of the dental implant and a size dimension of the dental implant.

18. The system of claim 16, wherein one of the at least two features of the dental implant is an x-y location of the surface of the dental implant.

19. A method of making a patient-specific prosthetic restoration dental component using scan data of a dental implant pre-positioned in bone within a mouth of a patient to develop a virtual model for use in a virtual design process, comprising:

receiving, by a computer, scan data of the mouth of the patient including a surface of the dental implant, the scan data including information corresponding to a scannable code on the surface of the dental implant, wherein the scannable code provides information regarding an anti-rotational feature of the dental implant;

providing, by a computer display, a display of a virtual model of at least a portion of the mouth of the patient;

using, by the computer, the information corresponding to scanning of a scannable code to position a virtual implant within the virtual model and determine an angular orientation of the anti-rotational feature in the virtual model;

developing, by the computer using the virtual model, the patient-specific prosthetic restoration dental component to be placed on the dental implant; and providing instructions to make the patient-specific prosthetic restoration dental component.

20. The method of claim 19, wherein the scan data comprises information relative to an interface coordinate system of the virtual model, a type of connection to the patient-specific prosthetic restoration dental component, an orientation of the anti-rotational feature of the dental implant, and information relative to a seating diameter of the dental implant, wherein the scannable code includes a circumferentially extending marker having a radius of curvature that is centered around a central axis of the dental implant, and wherein the radius of curvature provides a position of the central axis to assist with the virtual design process.

21. A system of using scan data of a dental implant pre-positioned in bone within a mouth of a patient to develop a virtual model for use in a virtual design process, comprising:

an input configured to receive scan data of the mouth of the patient including a surface of the dental implant, the scan data including information corresponding to a scannable code on the surface of the dental implant; and a computer configured to develop a virtual model of at least a portion of the mouth of the patient and use the scan data to locate a virtual implant within the virtual model, wherein the scannable code includes a circumferentially extending marker and wherein a radius of curvature of the circumferentially extending marker provides a position of a central axis of the dental implant.

* * * * *